United States Patent [19]

Garabedian

[11] Patent Number: Plant 5,906

[45] Date of Patent: Mar. 17, 1987

[54] PLUM TREE, "JOHN-JOHN"

[76] Inventor: John M. Garabedian, 3104 E. Huntington Blvd., Fresno, Calif. 93702

[21] Appl. No.: 766,553

[22] Filed: Aug. 19, 1985

[51] Int. Cl.[4] ..... A01H 5/03
[52] U.S. Cl. ..... Plt./38
[58] Field of Search ..... Plt./38

*Primary Examiner*—Robert E. Bagwill

*Attorney, Agent, or Firm*—Worrel & Worrel

[57] ABSTRACT

A new and distinct variety of plum tree which is somewhat similar to the Laroda Plum Tree (unpatented), with which it bears fruit which is of similar physical characteristics but which is distinguished therefrom by bearing fruit which ripens approximately 7 to 10 days before the fruit of the Laroda Plum Tree (unpatented) and which further is somewhat larger in size, more richly colored, and of a milder flavor.

1 Drawing Figure

BACKGROUND OF THE NEW VARIETY

The present invention relates to a plum tree, designated varietally by the name "John-John", and more particularly to a plum tree which bears a dark Purplish-Red fruit which ripens approximately 7 to 10 days before the fruit of the Laroda Plum Tree (unpatented), but which is distinguished therefrom in being somewhat larger on the average, more fully colored, and of a milder "less acidic" flavor.

For many years, the applicant has grown large acreages of fruit trees and has constantly sought to produce improved varieties thereof. One of the procedures used by the applicant to produce new fruit trees is to germinate thousands of seeds of unknown parentage, to grow the resulting seedlings to maturity, and then to evaluate the resultant trees and their fruit. The subject variety of this application is a result of one of these many randomly-pollinated seedlings of unknown parentage. The subject plum tree was originated in 1977 on the applicant's ranch near the corner of Kings Canyon Road and Fowler Avenue, Fresno, County of Fresno, State of California. The seedling of the present variety was germinated by the applicant and grown with thousands of other seedlings on his ranch near the intersection of the designated Kings Canyon Road and Fowler in the City of Fresno, until its unique qualities were detected and appreciated. The applicant then asexually reproduced the new variety in 1981, by grafting a scion of the new and distinct variety from the seedling onto standing seedling trees at the aforementioned orchard and observed the grafts to determine whether the characteristics observed in the original seedling were present. The grafted progeny were grown at the designated farm until it was determined that the new variety dependably and accurately reproduced the superior characteristics observed by the applicant in the original seedling.

As will subsequently become apparent, the instant variety of plum tree is somewhat similar to the Laroda Plum Tree (unpatented), with which it appears most nearly similar. However, the present variety of plum tree is harvested some 7 to 10 days prior to the Laroda Plum Tree, and in addition the fruit of the subject variety is somewhat larger on the average, is more richly colored, and has a less acidic flavor than the fruit of the Laroda.

BRIEF DESCRIPTION OF THE DRAWING

The accompanying drawing is a color photograph of a characteristic twig bearing typical leaves, a cluster of two plums showing their external coloration sufficiently matured for harvesting and shipment, two mature plums of the color when matured on the trees, a plum halved transversely of the suture plane to illustrate the flesh coloration, and five stones, all of the subject variety.

DETAILED DESCRIPTION

Referring more specifically to the pomological details of this new and distinct variety of plum tree, the following has been observed under the ecological conditions prevailing in the designated orchard near Fresno, Calif. All major color code designations are by reference to the Munsell Limit Color Cascade, hereinafter referred to as "MCC". Common descriptive color names are also used occasionally.

TREE

Size: Medium to large, depending upon pruning practices.
Vigor: Vigorous.
Figure: Upright, spreading, dense and vase-formed.
Productivity: Very productive.
Regularity of bearing: Regular.
Trunk:
- *Thickness.*—Medium.

Branches:
- *Thickness.*—Medium.
- *Texture.*—Medium.
- *Color.*—Gray.

LEAVES

Shoot:
- *Size.*—Medium to large.
- *Length.*—11.47±1.90 cm.
- *Width.*—4.51±0.61 cm.
- *Form.*—Oval to slightly obovate, acuminate, pointed.
- *Thickness.*—Medium.
- *Color.*—Ventral Surface — Green (MCC 21-15 to 20-14); Dorsal Surface — lighter and more Grayish-Green.

*Texture.*—Nearly smooth.
*Marginal form.*—Crenate.
*Petiole.*—Length — short to medium; Thickness — medium.
*Glands.*—Variable in number from 2 to 4; small, globose, green, opposite, positioned at the base of the blade or occasionally on the petiole when there are 3 or 4 glands.
*Stipules.*—Lacking.

Spur:
*Size.*—Small to medium.
*Length.*—10.36±1.57 cm.
*Width.*—3.29±0.49 cm.
*Form.*—Narrow and slightly obovate, acuminate, pointed.
*Base.*—Narrowly acuminate.
*Thickness.*—Thin to medium.
*Color.*—Ventral Surface — Dark Green (MCC 20-14 to 21-15); Dorsal Surface a lighter, grayer green.
*Texture.*—Nearly smooth.
*Marginal form.*—Finely crenate.
*Petiole.*—Length — short; Thickness — slender to medium.
*Glands.*—Variable in number, from 0 to 3; small, globose, green, opposite, usually positioned at the base of the blade.
*Stipules.*—Lacking.

Flower buds: Small, medium, plump, free, medium brown, and glabrous.

Flowers: Medium in size and white.
*Date of first bloom.*—Feb. 18, 1984.
*Date of full bloom.*—Feb. 28, 1984; an average date of bloom as compared with other varieties.

FRUIT

Maturity when described:
*Firm ripe for eating.*—July 6.

Size: Uniform; medium to large.
*Axial diameter.*—5.37±0.32 cm.
*Diameter transverse in suture plane.*—5.71±0.25 cm.
*Diameter transverse in cheek plane.*—6.04±0.36 cm.

Form: Uniform, although occasionally slightly variable; slightly unsymmetrical; globose to slightly oblate; one half of the subject variety often is larger apically.

Suture: An inconspicuous shallow groove extending from the base to the apex; there is a very slight depression beyond the pistil point.

Ventral surface: Rounded slightly, and lipped throughout.

Cavity: Rounded and slightly elongated in the suture plane, with the suture showing on one side.
*Depth.*—0.73±0.17 cm.
*Breadth.*—2.25±0.17 cm.
*Markings.*—None.

Base: More or less truncated.

Apex: Short; rounded to truncated, often oblique dorsally; occasionally depressed.

Pistil point: Apical.

Stem:
*Length.*—2 cm.; stout.

Skin: Medium in thickness; tough in texture; bitter to the taste; tenacious to the flesh; no observed tendency to crack.
*Down.*—Wanting.
*Color.*—Dark Purplish-Red (MCC 41-15 to 43-16); Ground Color — Brownish Tan (MCC 31-11); surface color may vary where the particular surface area has been covered by a leaf. Bloom — medium to heavy; Color — Blue-Gray (MCC 4-5).
*Dots.*—Numerous in number, regularly shaped, small, Light Brown; more numerous in number on the cheeks, shoulders, cavity, and along the suture; most numerous dorsally.

Flesh:
*Color.*—Light Amber Yellow (MCC 30-4); a slight reddish tinge persists next to the skin apically.
*Surface of the pit cavity.*—Darker in color than the flesh immediately adjacent thereto.
*Amygdalin.*—Scant.
*Juice.*—Production — moderate to rich.
*Texture.*—Firm and meaty.
*Fibers.*—Few, fine, and tender.
*Ripening.*—Even.
*Flavor.*—Mild to sub-acid.
*Aroma.*—Wanting.
*Eating quality.*—Good.

Stone: Semi-freestone.
*Size.*—Medium to large.
*Length.*—2.20±0.14 cm.
*Breadth.*—1.90±0.11 cm.
*Thickness.*—1.09±0.07 cm.
*Form.*—In the cheek view, a broad oval, to very slightly obovate; occasionally nearly round; usually broadly necked basally.
*Hilum.*—Narrow and oblong.
*Apex.*—Rounded, occasionally with or without a short, usually blunt tip.
*Sides.*—Variable, occasionally equal or slightly unequal.
*Surface.*—Irregularly furrowed near the base, with a marked ridge medianly on the cheeks.
*Ridges.*—Positioned toward the base.
*Ventral edge.*—Thin, without wing throughout.
*Dorsal edge.*—Narrow, with deep, broad grooves; positioned above center.
*Color of stone.*—Light Brown (MCC 31-3).
*Tendency to split.*—Not observed.

Use: Market and dessert.

Keeping quality: Good.

Resistance to insects: Medium.

Resistance to diseases: Medium.

Shipping quality: Good.

Although the new variety of plum tree possesses the described characteristics as a result of the growing conditions in Fresno County, Calif., in the central part of the San Joaquin Valley, it is to be understood that variations of the usual magnitude in characteristics incident to growing conditions, fertilization, pruning and pest control are to be expected.

Having thus described and illustrated my new variety of plum tree, I claim:

1. A new and distinct variety of plum tree substantially as illustrated and described which is most closely similar in tree and fruit characteristics to the Laroda Plum Tree (unpatented), and from which it is distinguished by bearing fruit which ripens approximately 7 to 10 days before the fruit of the Laroda Plum Tree, and which is further distinguished from the Laroda Plum Tree by being somewhat larger on the average, more richly colored, and milder and less acidic in flavor.

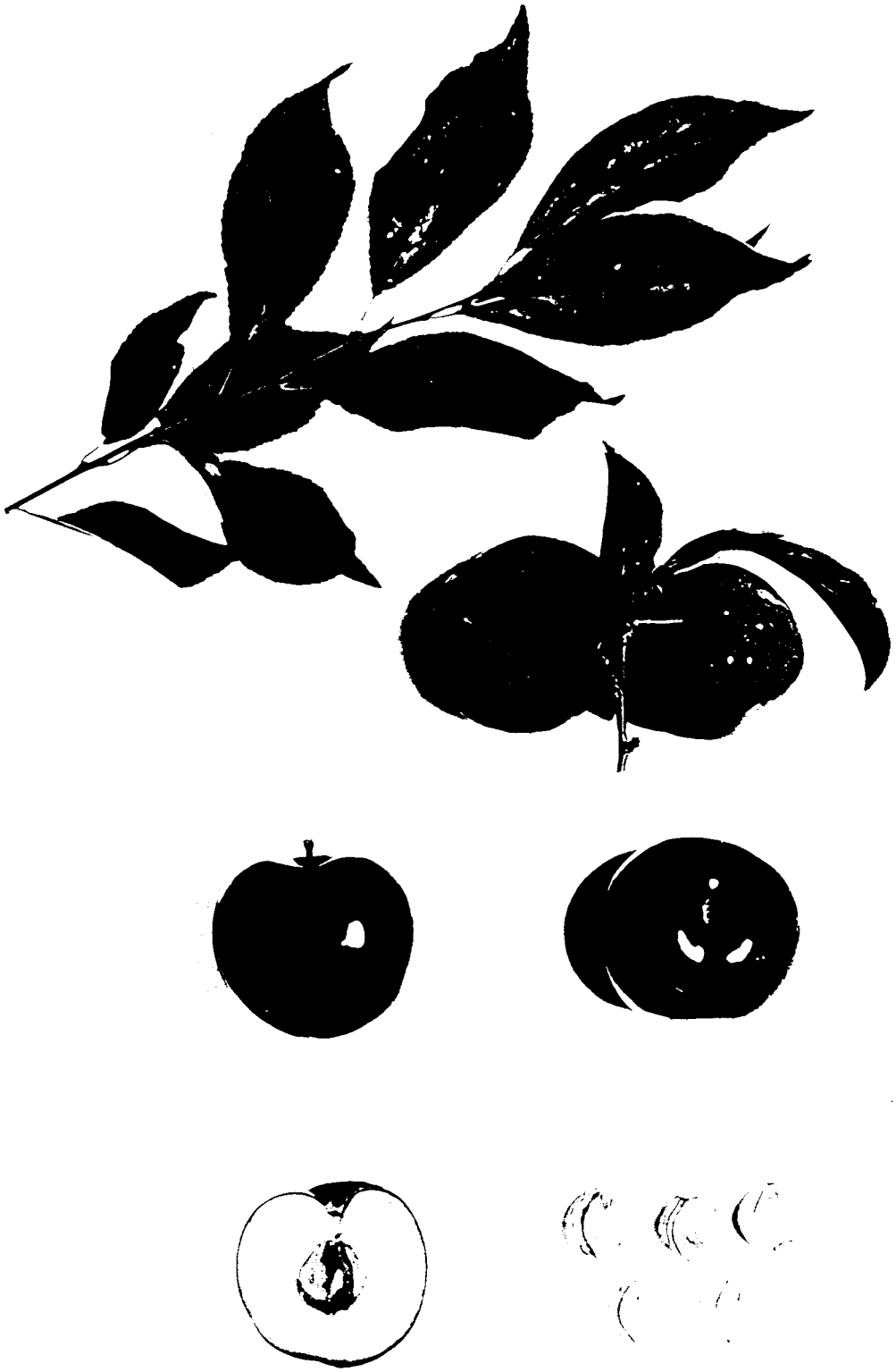

* * * * *